(12) United States Patent
Battle

(10) Patent No.: US 7,465,089 B2
(45) Date of Patent: Dec. 16, 2008

(54) PROTECTIVE COVERINGS FOR RADIOLOGICAL EQUIPMENT

(76) Inventor: Ronald K. Battle, 453 Spratley Cir., Newport News, VA (US) 23602

(*) Notice: Subject to any disclaimer, the term of this patent is extended or adjusted under 35 U.S.C. 154(b) by 24 days.

(21) Appl. No.: 11/599,144

(22) Filed: Jan. 4, 2007

(65) Prior Publication Data

US 2008/0165915 A1 Jul. 10, 2008

(51) Int. Cl.
*H05G 1/00* (2006.01)
*H05G 1/60* (2006.01)

(52) U.S. Cl. ............... 378/204; 378/4; 378/210
(58) Field of Classification Search ............. 378/4, 378/20, 209, 204, 210; 5/600; 128/849
See application file for complete search history.

(56) References Cited

U.S. PATENT DOCUMENTS 6,857,778 B2 * 2/2005 Mun et al. ............ 378/206

2006/0243284 A1 * 11/2006 Malmberg et al. ......... 128/849

* cited by examiner

*Primary Examiner*—Irakli Kiknadze
(74) *Attorney, Agent, or Firm*—Goldizen & Associates; Bradley D. Goldizen

(57) ABSTRACT

A disposable plastic covering includes a seal region and an apron region for use in directing fluids away from an interior region of the machine to prevent the fluids from entering a CT machine. The covering includes an inert adhesive material for securing a seal. The adhesive material fastens the seal region of the plastic covering across an opening between an external casing and a window arranged above a moving ring upon which an X-ray emitter and detector are arranged. The apron region of the plastic covering extends from within a central opening of the CT machine to direct fluids from within the machine to an exterior of the machine. A second plastic covering is arranged on an opposite side of the window and seals the second seam. A further embodiment includes a pouch region in the disposable plastic covering for directing fluid therein. An additional covering is provided for controls of the machine.

20 Claims, 6 Drawing Sheets

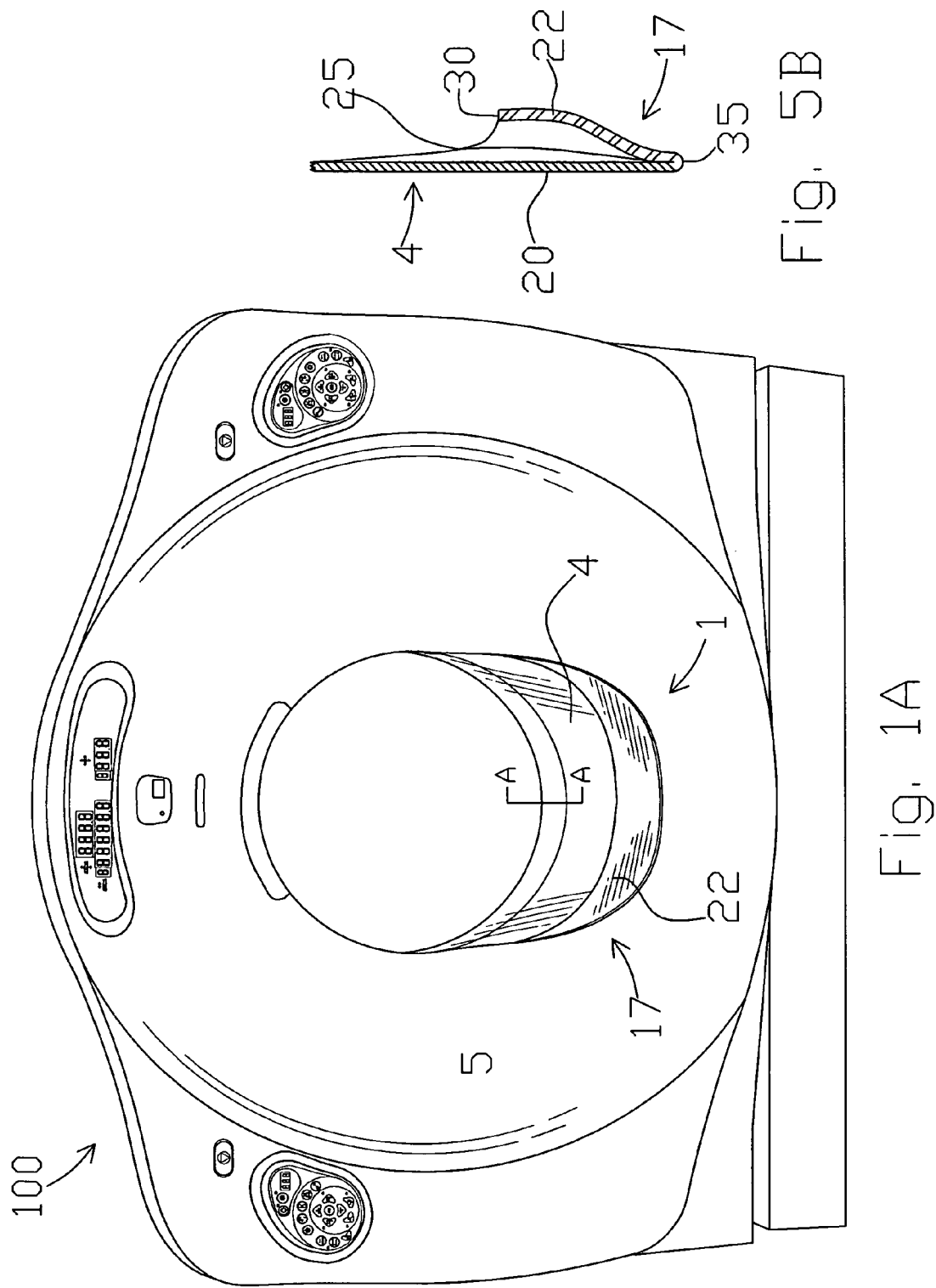

PROTECTIVE COVERINGS FOR RADIOLOGICAL EQUIPMENT

There are no related patent applications.

The subject matter of the present invention did not receive federal government research and development funding.

TECHNICAL FIELD

The present invention is generally related to protective coverings for radiological equipment and prevents fluids from entering the inner workings of a CAT or CT machine. More specifically, the present invention is directed towards a removable, replaceable guard that seals openings and directs body fluids and other like substances away from the machine. The present invention provides a disposable covering for protecting a gantry of a radiological machine.

BACKGROUND OF THE INVENTION

A computerized axial tomography scan is commonly known as a CAT scan or CT scan. The CT scanning machine uses X-rays to make detailed pictures of various structures inside of a patient's body. The CT machine looks like a giant doughnut having a central opening and being tipped on its side. The machine includes a plastic case or covering that protects the internal workings of the machine. Typically, this case is provided in two halves on opposite sides of the central opening. An X-ray tube is mounted on a movable ring around the edges of the central opening. The ring also supports an array of X-ray detectors arranged directly opposite the X-ray tube. A motor turns the ring so that the X-ray tube and the X-ray detectors revolve around the body. Each full revolution of the ring causes the X-ray tube and the X-ray detectors to scan a narrow, horizontal "slice" of the body. A clear plastic or Mylar covering, referred to hereinafter as a "window", protects the movable ring and it associated parts and is arranged between two halves of the plastic case. The window is located between two metallic rings that are arranged between the halves of the case and is removable. The flexible, removable window is situated between the two halves of the CT scanner and is designed to prevent moisture damage and body fluid contamination to the internal components of the CT unit. In some CT scanners, the window which allows the emission of coned X-ray beams may comprise plastic or other substances.

A table or platform is associated with the CT machine and slowly moves through the hole in the machine as the patient rests thereon. The control system moves the platform farther into the hole so that the tube and detectors can scan the next slice of the patient's body. During a CAT scan, a patient lies on the table while pictures of the internal structure being viewed are generated. The CT scanner sends X-ray pulses through the body area being studied. Each pulse lasts less than a second and takes a picture of a thin slice of the area of the body. The X-ray pictures are saved on a computer and combined with the aid of a computer to generate cross-sectional views and three-dimensional images the patient's organs and body structures. A CAT scan is used to define normal and abnormal structures in the body and/or assist in procedures by helping to accurately guide the placement of instruments or treatments.

In each of the pictures created during the CAT scan, the body is seen as an X-ray slice of the body, which may be recorded on film, as a digital image for viewing on computer monitors or preserved on other electronic storage media. This recorded image is called a tomogram. "Computerized Axial Tomography" refers to the recorded tomogram "sections" at different levels of the body. The body is seen on CAT scan slices in a similar fashion from the skin to the central part of the body being examined. When these levels are further "added" together, a three-dimensional picture of an organ or abnormal body structure can be obtained.

During the CT process, patients are often given an oral or intravenous dye that acts as a contrast material to aid in the evaluation of a patient and optimize the performance of the machine. This contrast material is very sticky which creates difficulty in cleaning it up after a spill has occurred during the examination process. Moreover, this material may cause the patient to become nauseous and regurgitate which tends to soil the machine. In fact, patients who require CT scans are often sick, injured, or may become ill during the process resulting in body fluids, or like substances, from the patient being dispersed onto the CT machine. Since the plastic casing and the window are not integrally sealed together, there exist two unsealed seams on opposite sides of the window into which contrast materials, body fluids or like substances may seep. Thus, these fluids may enter either of these seams and render the machine inoperable or contaminate the inner workings of the machine with body fluids.

BRIEF SUMMARY OF THE INVENTION

In one embodiment, the present invention is a disposable plastic covering that includes an inert adhesive material and semi-rigid seal that prevents fluids from entering the internal workings of a CT machine. The adhesive material fastens the seal region of the plastic covering across an opening between the plastic case and window arranged above the moving ring. An apron region of the plastic covering extends from within the central opening to direct fluids from within the machine. A second plastic covering is arranged on an opposite side of the window and seals the second seam. Either or both plastic coverings may include a pouch or pocket arranged at a bottom thereof for fluid collection and to further prevent spillage onto the scanner.

In another embodiment, in addition to the first, a disposable plastic covering is provided as an overlay for controls on the CT machine. In a preferred embodiment, the disposable plastic covering includes a plurality of overlays which may individually peeled or stripped from the disposable plastic covering, as necessary.

It is an object of the invention to provide a disposable plastic covering, a portion of which is secured above a moving ring of a CT scan machine, such that a seam that exists between an external casing of the CT scan machine and between a window of the CT scan machine is covered to prevent fluid from entering the machine.

It is another object of the invention to provide a cost effective means for preventing breakdowns of CT machines caused by fluid entering an unsealed region thereof.

It is a further object of the invention to provide a protective overlay for controls on a CT machine.

It is an additional object of the invention to provide a means of reducing the spread of possible bio-hazard contaminants from a CT machine to technologists and patients. Thus, the present invention is a protective covering that is easily replaceable and a cost-effective method of reducing or preventing the spread of disease.

It is an added object of the invention to increase staff efficiencies of radiological personal by reducing cleaning and decontamination times when spills occur.

It is a supplemental object of the invention to prevent the introduction of biological hazardous agents and cleaning fluids into the gantry controls. This in turn, reduces electronic failure of the CT scanner and prevents the breeding and spreading of harmful pathogens.

The above and further objects, details and advantages of the invention will become apparent from the following detailed description, when read in conjunction with the accompanying drawings.

BRIEF DESCRIPTION OF THE DRAWINGS

FIG. 1A is a perspective view of a first protective covering arranged within a CT scan machine.

FIG. 5B is as cross section view of FIG. 5B taken from line C-C of FIG. 5A.

DETAILED DESCRIPTION OF THE INVENTION

Figure 2:
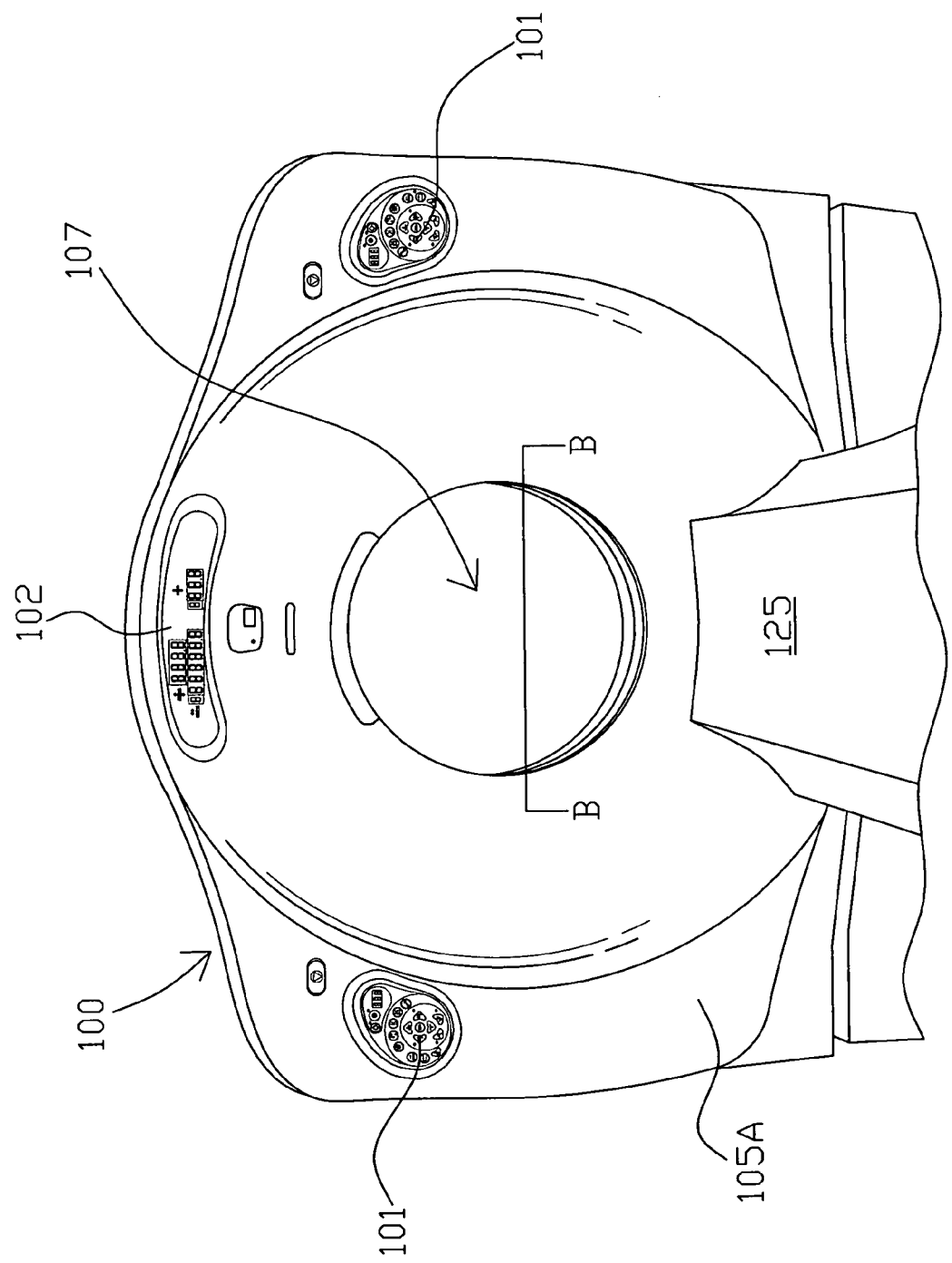
FIG. 2 is a prior art CT scan machine.
Figure 8:
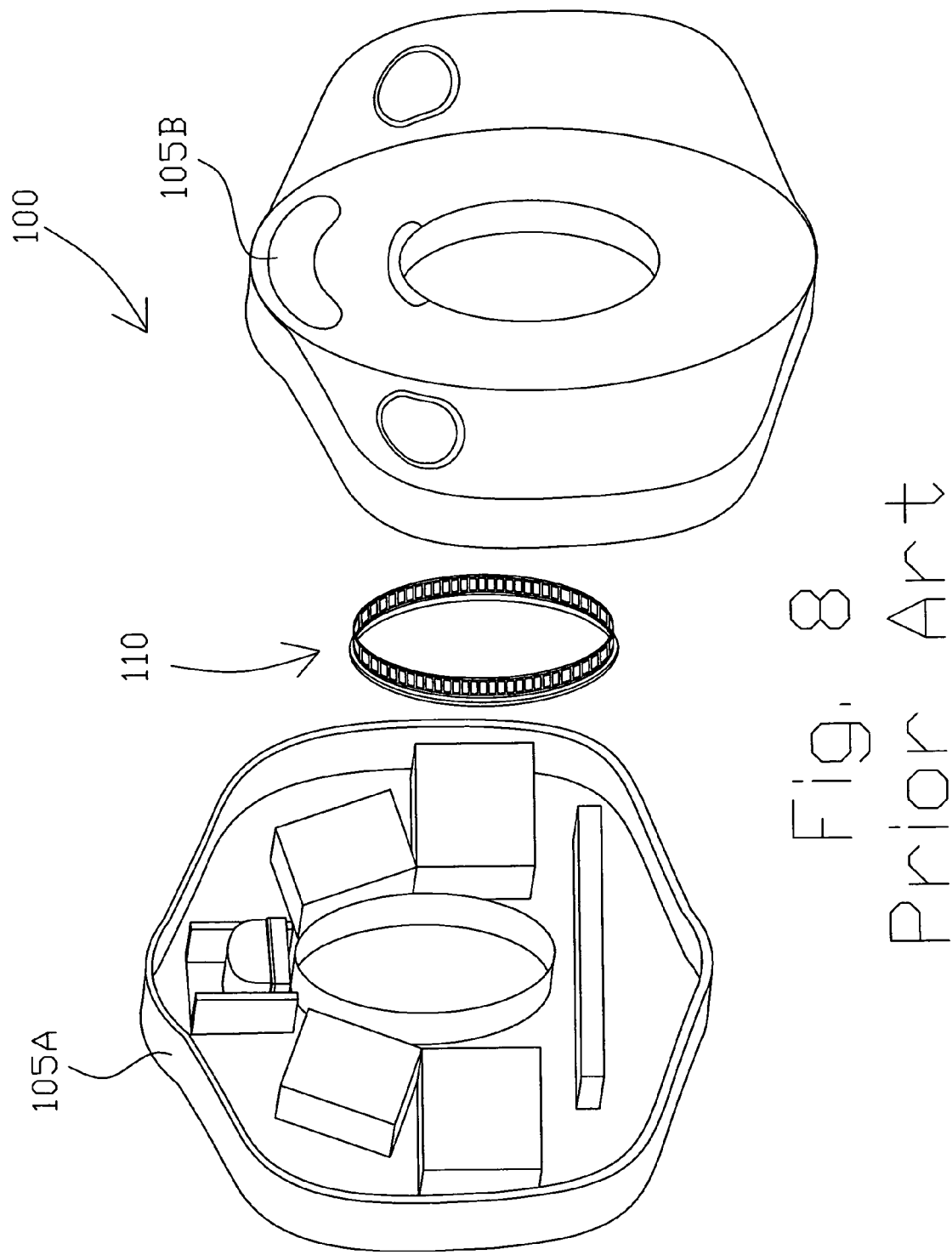
FIG. 8 is an exploded view of the prior art device shown in FIG. 2.

FIG. 2 shows a prior art CT scan machine 100 and associated table 125. The CT scan machine 100 includes a plurality of indicator lights 102 arranged above an inner opening 107 through which a patient or an area of the patient's body is passed. Controls 101 are arranged on opposite sides of the CT scan machine 100. A bed 125 is provided for passing the patient or his viewed part of body into the opening 107. As more clearly shown in the exploded view of FIG. 8, the CT scan machine 100 includes an external casing 105 that collectively comprises two halves 105A, 105B which are arranged on opposite sides of a movable ring 110. The halves of the external casing 105 protect the inner workings of the machine. For ease in understanding the invention, the other internal workings of the machine are not portrayed in FIG. 8.

Figure 7:
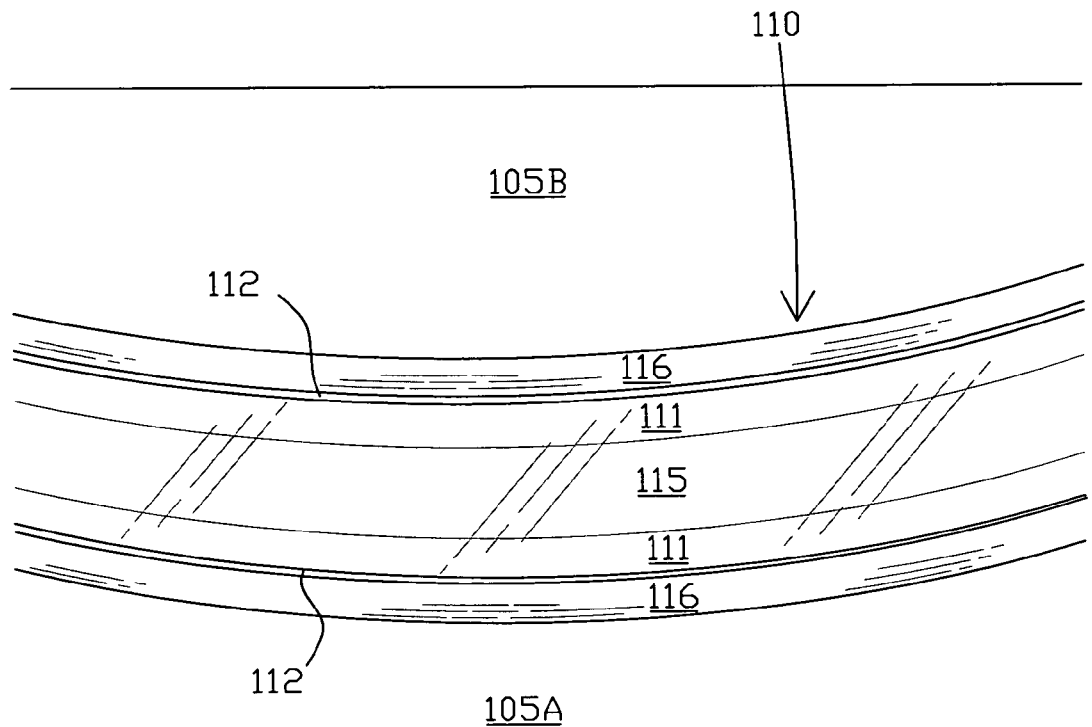
FIG. 7 is a sectional view of a movable ring taken from line B-B of FIG. 2.

FIG. 7 is a view of the movable ring 110 and external casing 105 taken from line A-A of FIG. 2. As shown in this Figure, opposite sides of the casing 105A, 105B are arranged against a clear window 115 that may comprise mylar. The movable ring 110 is seated behind the clear window 115 which butts against two aluminum edges 116 of either casing half 105A, 105B without a seal. Window supporting members 111 are included below the clear window 115. The unsealed openings 112 on either side of the window 115 allow fluid to enter into the machine. X-rays are emitted through the window 115 and received to provide a sliced image of a body part. The aluminum edges are arranged on opposite sides of the window 115 against the external casing 105.

Figure 1B:
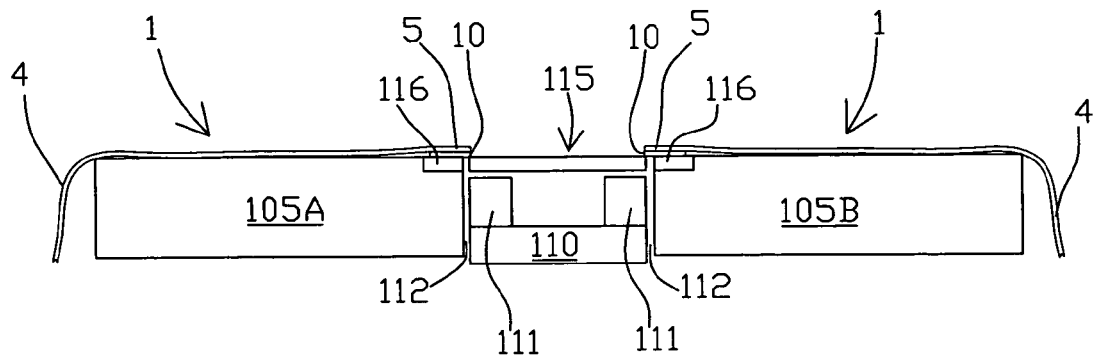
FIG. 1B is a cross section view of FIG. 1A taken at line A-A.

FIG. 1A is a perspective view of the CT scan machine of FIG. 2 and shown with the present invention, a protective covering 1. FIG. 1B shows two protective coverings 1 extending from opposite sides of the machine 100. Each protective covering 1 comprises a seal region 5 that overlaps one of the unsealed openings 112 and an apron region 4 of the invention extends outward from the central opening of the machine to direct fluids away from the machine. The protective covering 1 preferably comprises plastic material 3 that is pliable and is preferably between 1 and 6 millimeters in thickness. It should be noted that the thickness of the protective covering may be varied at different regions in the covering. In this embodiment, the protective covering 1 includes a pocket 17 for accepting fluids that are spilled upon the seal 5 or apron 4.

In FIG. 1A, the pocket 17 is shown being supported above the floor upon which the CT machine 100 rests. It is to be understood that an end of the protective covering 1 may extend to and rest upon the floor. As shown in the embodiment of FIG. 5B, the protective covering includes an apron 4 having a pocket 17 formed therein or attached thereto. In FIG. 5B, the pocket is formed by folding an end of the apron back onto itself. Seams 25 seal the front pocket sidewall 22 to the back pocket sidewall 20. The seams may be created using methods such as heat welding, sonic welding, adhesive disposed between the pocket sidewalls or other known methods. The pocket 17 includes a rounded bottom end 35 as shown. A lip 30 is formed at an upper edge of front pocket sidewall 22.

As shown in FIG. 1B, when in use, two protective coverings 1 are arranged to extend from the central opening of the CT machine outwards in opposite directions. As can be readily recognized from this view, the adhesive 10 extends across the unsealed opening 112 to seat the seal on an edge of the clear window 115 for each protective covering 1. Since the seal 5 is fluid impervious and is arranged with the adhesive 10 at top end of the protective covering 1 as shown, any spilled fluid is prevented from entering the machine 100 through the unsealed openings 112. Moreover, the fluid is directed outward to minimize the necessary parts that must be cleaned when a patient regurgitates.

Figure 3:
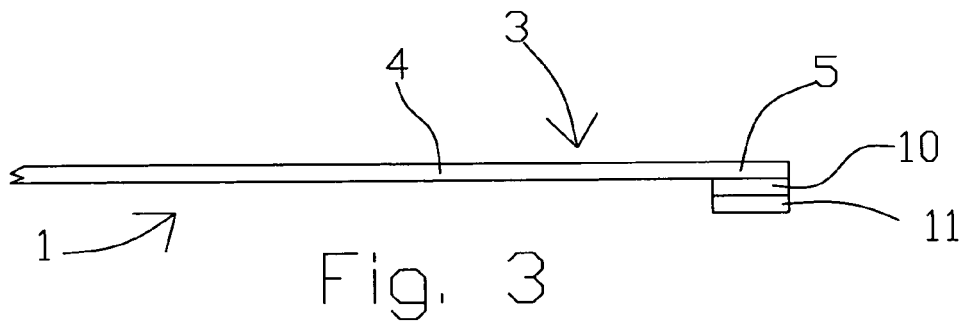
FIG. 3 is an elevation side view of the first embodiment shown in FIG. 1.
Figure 4:
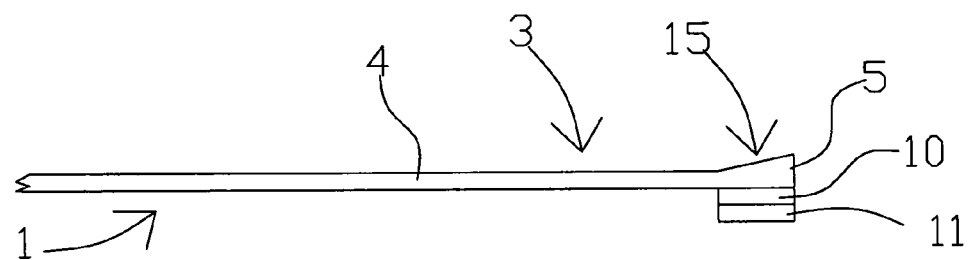
FIG. 4 is an elevation side view of an additional embodiment showing the seal region having a different shape.

FIGS. 3 and 4 show two embodiments of the invention from an elevated view. FIG. 3 depicts the invention in its simplest form only the apron 4 and seal 5 are included. An adhesive strip 10 that may have a width that spans an unsealed opening 112, or which is greater in width than the opening 112, is included on a back side of the seal that comes into contact with the machine. Removable backing 11 is arranged on a side of adhesive strip 10 opposite seal 5. Otherwise, the adhesive strip may be shorter in width than the unsealed opening but arranged to fasten the furthermost edge of the seal against an exposed surface of the clear window near the edge of the clear window that abuts the unsealed opening.

FIG. 4 is another embodiment of the invention wherein the front or exposed side 15 of the seal 5 is sloped to aid in flowing liquids from the seal 5 and towards the apron region 4. This embodiment may further include the pocket 17 as shown in FIG. 1A and described above.

Figure 5A:
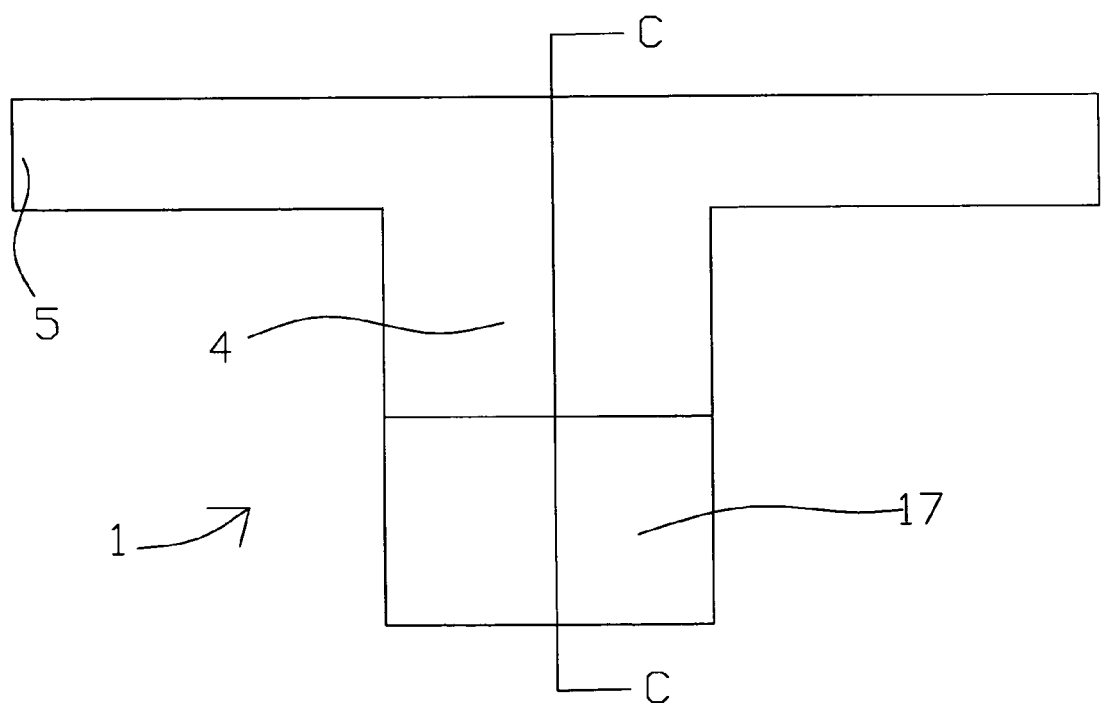
FIG. 5A is a plan view of the first protective covering shown in FIG. 1.

FIG. 5A is a plan view showing the invention. As can be seen in this figure, the invention comprises a seal portion 5 that is preferably larger in width than an apron portion. The seal portion 5 includes a thin strip of adhesive material 10 deposited on one side thereof as discussed above. Removable backing 11 is arranged on the adhesive material 10 to ensure that no foreign matter comes into contact with the adhesive before the device is placed in the machine. A technician removes this backing prior to use.

Figure 6A:
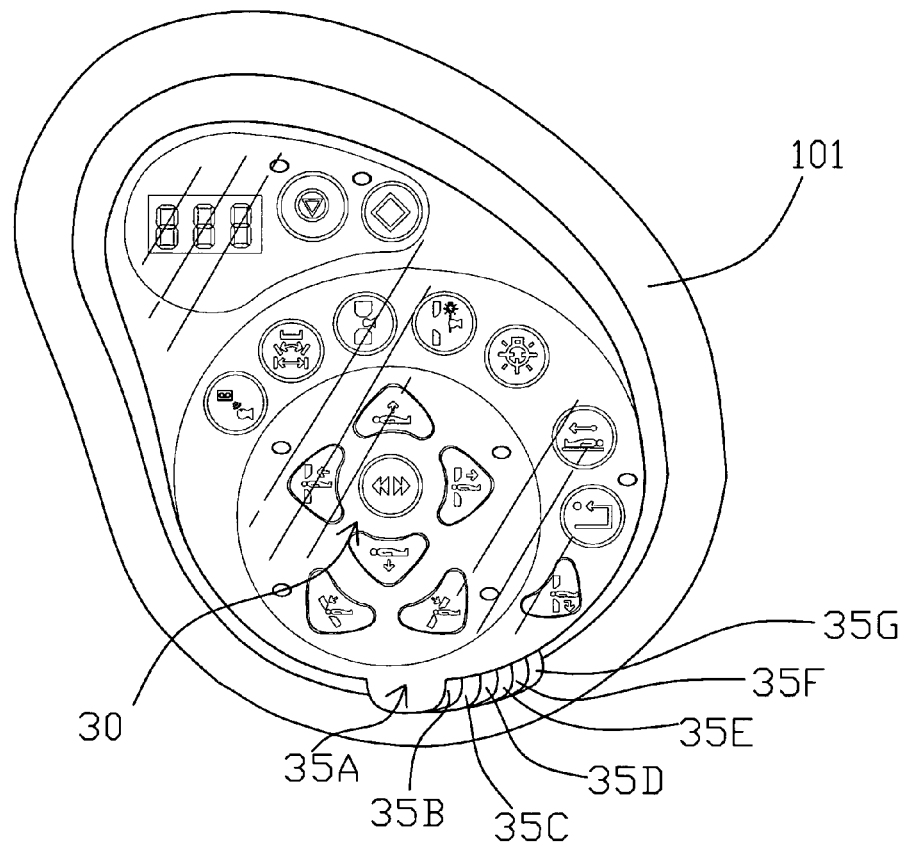
FIG. 6A is a further embodiment of the invention showing "peel off" protective coverings arranged across controls to the CT scan machine.
Figure 6B:
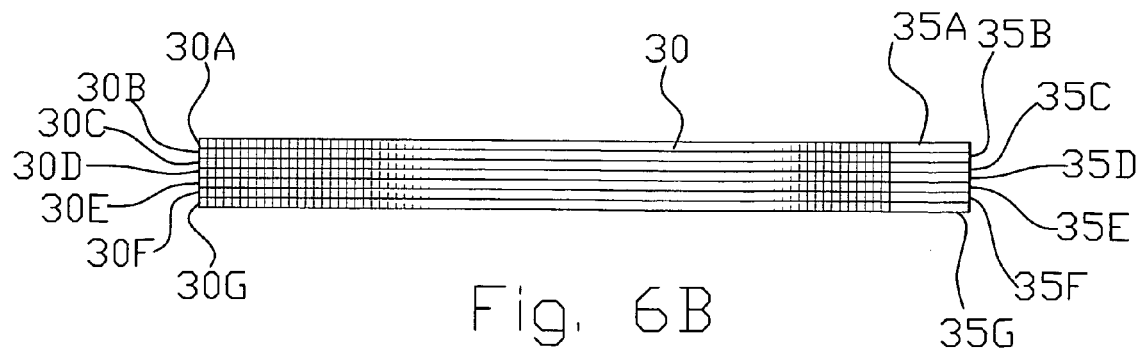
FIG. 6B is a cross section view of FIG. 6A.

FIG. 6A is a perspective view of an overlay for protecting the control buttons of the CT machine and includes a plurality of "tear-off" layers, collectively referred to as element 30. Each layer 30 includes a tab 35 that partially overlaps an underlying tab 35. The tabs 35 are sequentially grasped by the user and a particular overlay associated with that particular tab is removed when the tab is pulled. The overlay 30 comprises a plurality of layers indicted in FIG. 6B as layers 37A through 37G. Each layer utilizes static electricity or static cling to hold it to the layer below. The bottom layer adheres to the controls 101 in a manner similar to self-adhering window stickers. In this manner, the overlay may comprise vinyl layers that are stacked as shown in FIG. 6B.

While the invention has been described with respect to preferred embodiments, it is intended that all matter contained in the above description or shown in the accompanying drawings shall be interpreted as illustrative and not in limiting sense. From the above disclosure of the general principles of the present invention and the preceding detailed description, those skilled in the art will readily comprehend the various modifications to which the present invention is susceptible. Therefore, the scope of the invention should be limited only by the following claims and equivalents thereof.

I claim:

1. In a radiology machine having a central opening and a rotating ring arranged inside of the central opening, said rotating ring including an X-ray tube and at least one X-ray detector arranged opposite the X-ray tube for taking at least an X-ray of a particular part of a patient's body, said radiology machine including an external casing that surrounds inner workings of the radiology machine, a clear plastic window of material through which X-rays emitted from the X-ray tube pass, said clear plastic window being abutted between opposite edges of the external casing to create two unsealed seams, a protective covering comprises:
    a sheet of fluid impervious material having a top and a bottom that forms an apron;
    a semi-rigid strip attached to the top of the fluid impervious material having a front side and a back side said front side being exposed to an interior of the central opening, said back side being in contact with the clear plastic window; and,
    an inert adhesive material arranged on the back side of the semi-rigid strip and atop one of the unsealed seams that exists between the external casing and the clear plastic window;
    wherein said apron extends from within the central opening to direct fluid, spilled therein, outwards from the central opening and away from the clear plastic window.

2. The protective covering of claim 1 further comprising pliable, plastic material having a thickness of between 1 and 6 millimeters.

3. The protective covering of claim 1 further comprising a pocket that accepts fluids that are spilled on either the semi-rigid strip or apron.

4. The protective covering of claim 3 wherein said pocket comprises a front sidewall and a rear sidewall, said front sidewall further comprising a lip.

5. The protective covering of claim 3 wherein said pocket is formed from a single sheet of pliable material that is overlapped.

6. The protective covering of claim 3 wherein said pocket comprises a seam arranged on opposite sides thereof.

7. The protective covering of claim 1 wherein said apron comprises a pocket.

8. The protective covering of claim 7 wherein said pocket extends to a floor upon which the radiology machine is arranged.

9. The protective covering of claim 1 wherein said semi-rigid strip includes a front side that is sloped at a downward angle towards the apron.

10. A protective covering for a radiology machine having a central opening and a rotating ring arranged inside of the central opening, said rotating ring including an X-ray tube and at least one X-ray detector arranged opposite the X-ray tube for taking at least an X-ray of a particular part of a patient's body, said radiology machine including an external casing that surrounds inner workings of the radiology machine, a clear plastic window of material through which X-rays emitted from the X-ray tube pass, said clear plastic window being abutted between opposite edges of the external casing to create two unsealed seams, said protective covering comprising:
    a pliable strip of plastic having a first end and a second end;
    a seal arranged at the first end of the pliable strip of plastic, said seal comprising an adhesive strip arranged above one of the unsealed seams and atop an edge of the clear plastic window; and,
    an apron extending from said seal and including the second end of the pliable strip of plastic.

11. The protective covering of claim 10 further comprising pliable, plastic material having a thickness of between 1 and 6 millimeters.

12. The protective covering of claim 10 further comprising a pocket that accepts fluids that are spilled on either the semi-rigid strip or apron.

13. The protective covering of claim 12 wherein said pocket comprises a front sidewall and a rear sidewall, said front sidewall further comprising a lip.

14. The protective covering of claim 12 wherein said pocket is formed from a single sheet of pliable material that is overlapped.

15. The protective covering of claim 12 wherein said pocket comprises a seam arranged on opposite sides thereof.

16. The protective covering of claim 10 wherein said apron comprises a pocket.

17. The protective covering of claim 16 wherein said pocket extends to a floor upon which the radiology machine is arranged.

18. The protective covering of claim 10 wherein said semi-rigid strip includes a front side that is sloped at a downward angle towards the apron.

19. In a radiology machine including an X-ray tube and at least one X-ray detector arranged opposite the X-ray tube for taking at least an X-ray of a particular part of a patient's body, said radiology machine further including an external casing that surrounds inner workings of the radiology machine and at least one control panel having controls for operating the radiology machine, a protective overlay comprises:
    a plurality of stacked sheets of clear plastic material that adhere to one another through static clinging, each sheets including a tab that is partially overlaid onto a tab of a lower sheet except for the last sheet in the stack which overlays onto the control panel.

20. The protective overlay of claim 19 wherein the clear plastic material is vinyl.

* * * * *